United States Patent
Cai et al.

(10) Patent No.: US 7,091,044 B2
(45) Date of Patent: Aug. 15, 2006

(54) PARTIAL MODULATION VIA PULSED FLOW MODULATOR FOR COMPREHENSIVE TWO-DIMENSIONAL LIQUID OR GAS CHROMATOGRAPHY

(75) Inventors: Huamin Cai, Houston, TX (US); Stanley Stearns, Houston, TX (US)

(73) Assignee: Valco Instruments Co., Inc., Houston, TX (US)

( * ) Notice: Subject to any disclaimer, the term of this patent is extended or adjusted under 35 U.S.C. 154(b) by 0 days.

(21) Appl. No.: 10/913,672

(22) Filed: Aug. 6, 2004

(65) Prior Publication Data

US 2005/0048662 A1    Mar. 3, 2005

Related U.S. Application Data

(60) Provisional application No. 60/498,821, filed on Aug. 29, 2003.

(51) Int. Cl.
*G01N 30/46*    (2006.01)

(52) U.S. Cl. .......................... 436/161; 436/53; 422/70; 422/89; 422/82; 73/23.41; 73/23.42; 73/61.55; 73/61.56; 95/86; 96/103; 96/104; 210/198.2; 210/656

(58) Field of Classification Search ................. 422/70, 422/89, 81, 82; 436/161, 52, 53; 73/61.55, 73/61.56, 23.41, 23.42; 210/656, 198.2; 95/82, 86, 89; 96/103, 104, 105, 106
See application file for complete search history.

(56) References Cited

U.S. PATENT DOCUMENTS

| | | | |
|---|---|---|---|
| 4,316,381 A * | 2/1982 | Woodruff | 73/31.05 |
| 5,135,549 A * | 8/1992 | Phillips et al. | 95/8 |
| 5,196,039 A | 3/1993 | Phillips et al. | |
| 5,492,555 A | 2/1996 | Strunk et al. | |
| 6,007,602 A | 12/1999 | Ledford, Jr. et al. | |
| 6,547,852 B1 | 4/2003 | Ledford, Jr. et al. | |
| 6,702,989 B1 | 3/2004 | Sacks et al. | |
| 6,706,534 B1 | 3/2004 | Sacks et al. | |
| 6,706,535 B1 | 3/2004 | Sacks et al. | |
| 2002/0148353 A1 | 10/2002 | Seeley | |
| 2003/0106363 A1 | 6/2003 | Sacks et al. | |
| 2003/0108448 A1 | 6/2003 | Sacks et al. | |
| 2003/0109054 A1 | 6/2003 | Sacks et al. | |
| 2004/0232366 A1* | 11/2004 | Seeley | 251/12 |

OTHER PUBLICATIONS

Philip J. Marriott, "Time-Resolved Cryogenic Modulation for Targeted Multidimensional Capillary Gas Chromatography Analysis", The Journal of Chromatography, 2000, 15-28, 892.

Philip J. Marriott et al., "An Analytical Study of Comprehensive and Targeted Multidimensional Gas Chromatography." Publication information unknown.

Matthias Pursch et al., "Modulation Techniques and Applications in Comprehensive Two-Dimensional Gas Chromatograpy (GCXGC)," Analytical Bioanalytical Chemistry, Jan. 9, 2002.

* cited by examiner

*Primary Examiner*—Jan M. Ludlow
(74) *Attorney, Agent, or Firm*—Crain, Caton & James, P.C.; James E. Hudson, III (57) ABSTRACT

This invention is a method and device for use with multi-dimensional chromatography that utilizes partial modulation. An analyte-bearing sample is subjected to a first dimension of chromatography. Thereafter the separated analyte-bearing sample is diluted with a modulated second carrier such at the analyte-bearing sample is not stopped or its temperature altered. The partially modulated analyte-bearing sample then feeds into a secondary column where the analyte-bearing sample is further separated.

7 Claims, 5 Drawing Sheets

PARTIAL MODULATION VIA PULSED FLOW MODULATOR FOR COMPREHENSIVE TWO-DIMENSIONAL LIQUID OR GAS CHROMATOGRAPHY

CROSS-REFERENCE TO RELATED APPLICATIONS

This application claims the benefit of U.S. Provisional Patent Application No. 60/498,821 entitled, "Partial Modulation via Pulsed Flow Modulator for Comprehensive Two-Dimensional Liquid or Gas Chromatography," filed on Aug. 29, 2003 in the U.S. Patent and Trademark Office.

STATEMENT REGARDING FEDERALLY SPONSORED RESEARCH OR DEVELOPMENT

Not Applicable.

BACKGROUND OF THE INVENTION

1. Field of the Invention

The present invention relates to two-dimensional chromatography. Specifically this invention relates to devices and method for performing two-dimensional liquid or gas chromatography with partial modulation.

2. Description of the Related Art

Two-dimensional chromatography is known in the art. The fields of both gas and liquid chromatography utilize two-dimensional separation techniques to analyze sample matrices contained in a sample analyte.

Comprehensive two-dimensional liquid or gas chromatography utilizes two orthogonal columns connected in series to separate compounds within a sample. The term "orthogonal" as used herein means that the columns separate compounds within a sample based on two different properties of the compounds. Ideally, the different properties are independent of each other, resulting in a lack of correlation between the retention time of the compound in the first column and its retention time in the second column. The stationary phase in the second column should yield a faster separation than that of the first column. In the prior art, a sample is injected into the injection port and integrated with the mobile phase. The mobile phase is necessary to introduce and transport the sample through the column. In gas chromatography, the mobile phase is generally an inert gas and is often referred to as the carrier gas. In liquid chromatography, the mobile phase is a liquid of low viscosity and is often referred to as the carrier fluid. Injection of the sample may be by a syringe or operation of a valve or valves connected to a source or loop, among other methods. As the mobile phase transports the sample through the first column, the compounds in the sample are separated based on a first property. In the prior art, the first-column separated sample-bearing carrier exits the first column and is thereafter trapped and held by operation of a modulator, which releases the first column separated sample-bearing carrier in "plugs" or "packets" to the second column. The period during which a packet of first column separated sample-bearing carrier enters the second column is typically measured in seconds and is referred to as the secondary retention time. A detector at the exit of the second column measures the intensity of compounds in each packet at the conclusion of the second separation.

Primary retention time and secondary retention time identify each compound in the sample-bearing carrier in three dimensions. Modeling of the data with intensity in three-dimensions displays quantitative and qualitative properties of the compounds within the sample.

In prior art two-dimensional gas chromatography, the sample-bearing carrier was fully modulated. U.S. Pat. No. 5,196,039 issued to Phillips et al. on Mar. 23, 1993 discloses a thermal modulator device and method of performing comprehensive multi-dimensional chemical separation using a first dimension of a two-dimensional chromatograph to generate a chromatogram in a time comparable to or even faster than prior practice while the second dimension generates multiple chromatograms each in a time comparable to the fastest prior art chromatography. The transfer of sample portions from the first dimension to the second dimension is by any one of several sample-bearing carrier modulation techniques wherein portions of sample-bearing carrier are accumulated between the first and second dimensions and transferred as very sharp concentration pulses.

An article entitled, "Time-resolved Cryogenic Modulation for Targeted Multidimensional Capillary Gas Chromatography Analysis" by Philip J. Marriott et al. was published in the *Journal of Chromatography* in 2000. The article discloses a method incorporating two directly coupled columns and employing a longitudinally modulated cryogenic trap located between the columns. A method termed "selected zone compression pulsing" is used. All of the first column effluent is passed to the second column. The times at which the modulation of the trap is performed determines which target solutes will be selected for enhanced separation, allowing almost instantaneous separation of selected zones in the second column.

U.S. Pat. App. Pub. No. US 2002/0148353 by Seeley published on Oct. 17, 2002 discloses a two-dimensional gas chromatograph with a primary column and dual secondary columns. Flow rates in the primary column are less than those in the secondary column due to an accumulation valve. The accumulation valve operates to accumulate the sample as it exits the primary column, and introduce the accumulated sample to the dual secondary columns. Typically the ratio of the combined dual secondary columns flow capacity to the primary column flow capacity is approximately between 10 to 1 and 30 to 1.

U.S. Pat. No. 6,007,602 issued to Ledford, Jr. et al. on Dec. 28, 1999 discloses an apparatus and a method for forming a chemical modulation of a substance present in a fluid stream. The apparatus utilizes a movable device, such as a movable heater, to induce changes in the retention of a chemical substance flowing through the modulator tube.

U.S. Pat. No. 6,702,989, issued to Sacks et al. on Mar. 9, 2004 and U.S. Pat. Nos. 6,706,534, and 6,706,535 both issued to Sacks et al. on Mar. 16, 2004 disclose a gas chromatography system having a computer-controlled pressure controller that delivers pressurized pulses to a column junction point of two series-coupled columns having different stationary-phase chemistries. Each pressurized pulse causes a differential change in the carrier gas velocities in the two columns, which lasts for the duration of the pressurized pulse.

Comprehensive 2-D chromatography with full modulation of the sample-bearing carrier is not without drawbacks as to temperature, size and power requirements of equipment, and time required for secondary dimension analysis. Each column is operated throughout a temperature range, which may be beyond the range of the modulator. In such cases, the sample-bearing carrier is removed from the higher-temperature environment of the first column to a second environment where full modulation occurs, then reintroduced to the higher temperature environment to pass through the second column. Such cooling and heating may alter the compounds within the sample-bearing carrier, skewing the results. Such a full modulator may require cryogenic cooling, restricting the size and portability. Finally, the secondary retention time for full modulation should be long enough for a full separation in secondary dimension.

It would be an improvement to the art to be able to sufficiently modulate an analyte-bearing sample to permit comprehensive 2-D liquid or gas chromatography which would not alter the chemical properties of primary separation and which would permit a shorter secondary retention time.

BRIEF SUMMARY OF THE INVENTION

Accordingly, it is an object of the present invention to provide a partial modulation device and method for use in multi-dimensional chromatography that:

possesses both a primary and secondary signal;
maintains resolution of the primary signal; and
permits a shorter secondary retention time.

This invention is a method and device for use with multi-dimensional gas or liquid chromatography that utilizes partial modulation. A sample-bearing first carrier is subjected to a first dimension of chromatography. Thereafter the primary-column separated sample-bearing first carrier is partially modulated, which occurs by modulation between two concentrations by dilution with a second carrier, which will be a carrier gas in gas chromatography and a liquid in liquid chromatography, such that the primary-column separated sample-bearing carrier is not stopped or its temperature altered. The second carrier may be, but is not required to be, of the same composition as the first carrier. The partially-modulated primary-column separated sample-bearing first carrier then feeds into a secondary column where the primary-column separated sample-bearing first carrier is further separated. A detector at the end of the secondary column is used to determine the intensity of compounds exiting the column.

DESCRIPTION OF THE INVENTION

Structure and Method

Figure 1:
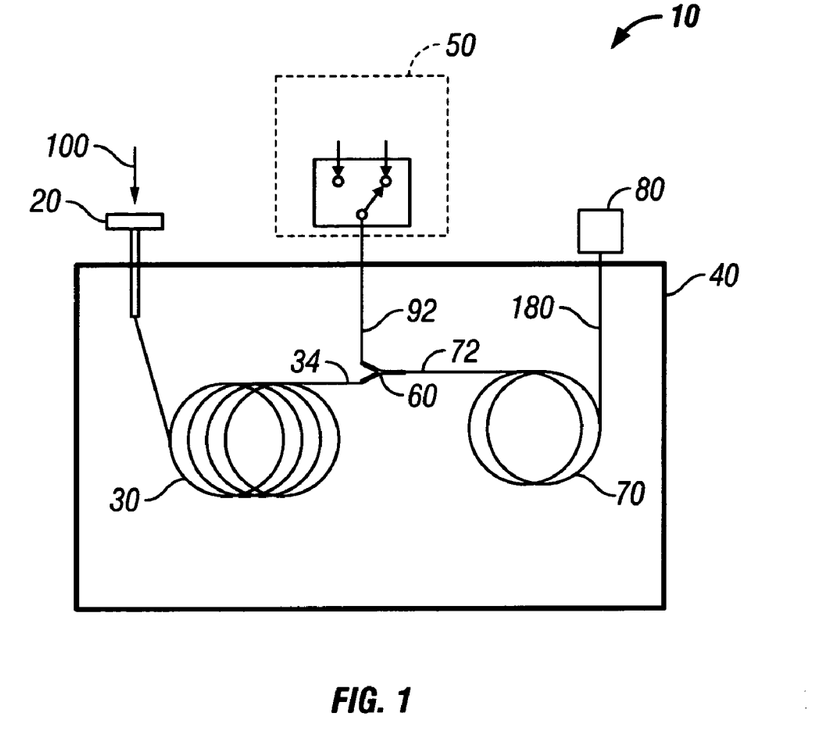
FIG. 1 is a schematic of the inventive chromatograph with partial modulation.

Referring to FIG. 1, a chromatograph with partial modulation is depicted as 10. The chromatograph 10, for liquid or gas, comprises an injector 20, a primary column 30, a modulator 50, a three-way connector 60, a secondary column 70, and a detector 80.

The sample-bearing first carrier 100 to be analyzed is introduced into primary column 30 by injector 20. In the preferred embodiment, for gas chromatography, primary column 30 is located within a thermal chamber 40, which maintains sample-bearing first carrier 100 at a predetermined temperature.

As sample-bearing first carrier 100 transverses primary column 30, various compounds within sample-bearing first carrier 100 linger in primary column 30 for differing lengths of time. The length of time in which a compound remains in primary column 30 depends upon its affinity for the stationary phase in that column. Compounds with less affinity for the stationary phase in primary column 30 will progress faster than compounds having an affinity for the stationary phase. Thus, various compounds exit primary column 30 at different points in time after their injection into primary column 30.

From primary column 30, a now primary-column-separated sample-bearing first carrier 100 enters three-way connector 60. Three-way connector 60 interfaces between primary column exit 34 and secondary column entrance 72. Preferably, three-way connector 60 is under the same conditions as primary column 40. In the preferred embodiment, for gas chromatography, three-way connector 60 is located in thermal chamber 40.

Figure 2:
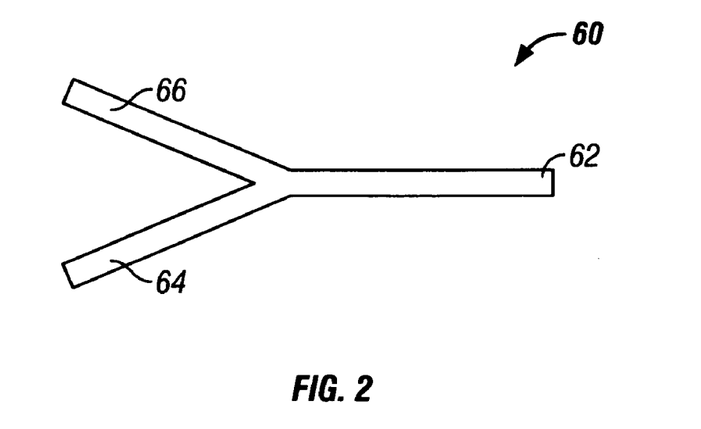
FIG. 2 is a top view of three-way connector.

As depicted in FIG. 2, in the preferred embodiment, three-way connector 60 is a press-on Y-connector having two entrance ports 64 and 66 and an exit port 62. There is an angle 68a between entrance port 64 and exit port 62 and an angle 68b between entrance port 66 and exit port 62. Angles 68a and 68b are greater than 90 degrees, that is each entrance port 64 and 66 is located at an obtuse angle from exit port 62.

Referring to FIGS. 1 and 2, primary column exit 34 is connected to one entrance port 64. Exit port 62 is connected to secondary column entrance 72. Therefore, the flow of primary-column-separated sample-bearing first carrier 110 is unobstructed between primary column 30 and secondary column 70.

Figure 3:
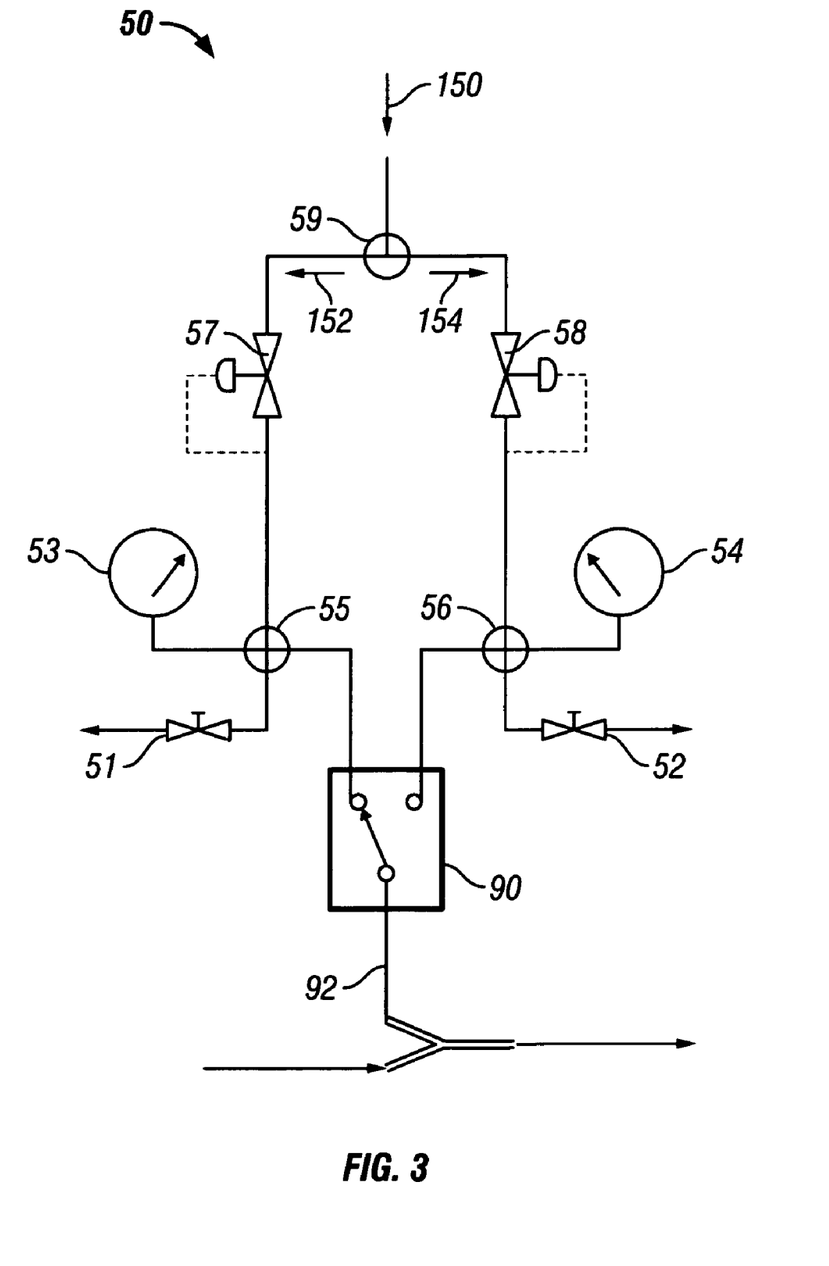
FIG. 3 is a schematic of the modulator.

Referring to FIG. 3, modulator 50 is depicted. In the preferred embodiment, modulator 50 includes a T-connector 59, through which a second carrier 150 is divided into two second carriers 152 and 154. The flow rate of second carrier 152 is adjusted downstream to be slower than the flow rate of the second carrier 154. Regulators 57 and 58, located along the path of second carrier 152 and 154, respectively, are adjusted to provide a slower flow rate to second carrier 152 than the flow rate of second carrier 154. In the preferred embodiment, regulators 57 and 58 regulate pressure for gas chromatography.

Each second carrier 152 and 154 passes through a cross connector 55 and 56 respectively. In the preferred embodiment, pressure gauges 53 and 54 are also connected to cross connectors 55 and 56 respectively to monitor the pressure of second carrier 152 and 154 respectively for gas chromatography. Each cross connector 55 and 56 also connects to a valve 51 or 52 respectively, the purpose of which is discussed below and which are needle valves in the preferred embodiment. The remaining terminal of each cross connector 55 and 56 connects to a valve 90.

Valve 90, which may be a fast solenoid switch, alternates the flow into a modulator exit 92 between slower second carrier 152 and faster second carrier 154. Modulator 50 therefore repeatedly and continuously cycles at a fixed rate of time between faster second carrier 154 and slower second carrier 152. Modulator exit 92 connects directly to entrance port 66 of three-way connector 60.

Needle valves 51 and 52 are used to vent second carrier 152 and 154, respectively. When slower second carrier 152 is directed to modulator exit 92 by valve 90, faster second carrier 154 is vented through needle valve 52. Likewise, when faster second carrier 154 is directed to modulator exit 92, slower second carrier 152 is vented through needle valve 51.

As previously discussed, the difference in flow rates between the slower second carrier 152 and the faster second carrier 154 is adjusted so that the flow rate of slower second carrier 152 is less than that of faster second carrier 154. The flow rate of slower second carrier 152 is set at a rate sufficient to prevent upstream contamination by primary-column-separated sample-bearing first carrier 110 in entrance port 66. Specifically, the flow rate of slower second carrier 152 should stop any part of primary-column-separated sample-bearing first carrier 110 from entering entrance port 66.

Modulator 50 may have alternative structures so long as the second carrier flow rate can be cycled between a faster and a slower flow rate. Alternative embodiments of modulator 50 include a pump (not shown), an impeller (not shown), or a valve that cycles between differently sized orifices (not shown). Other structures that allow cycling of the flow rate of the second carrier may also be used as a modulator (50).

Figure 4A:
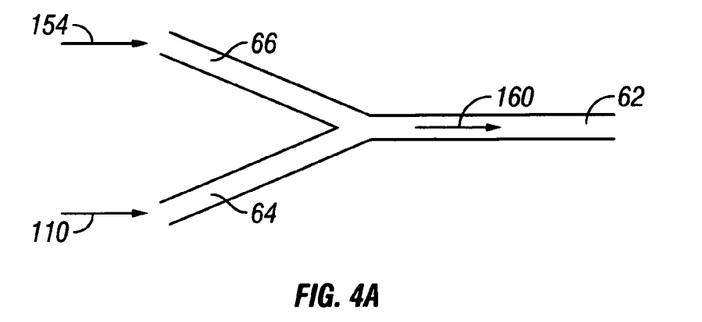
FIG. 4A depicts three-way connector with primary-column separated sample-bearing first carrier and higher flow rate second carrier entering connector.
Figure 4B:
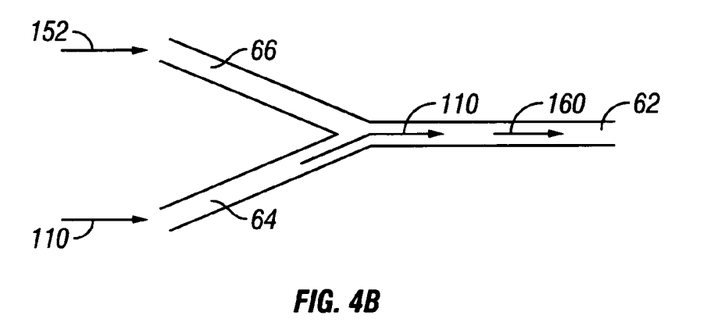
FIG. 4B depicts three-way connector with lower flow rate second carrier entering connector.
Figure 4C:
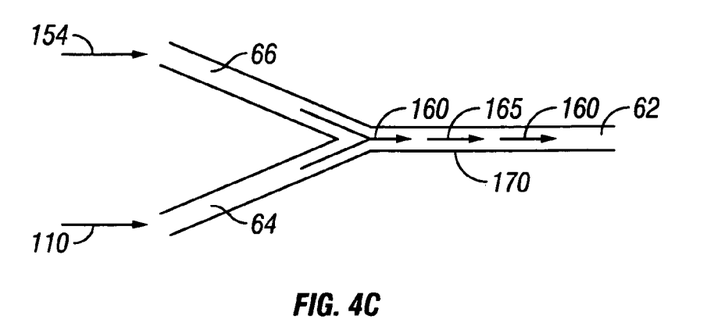
FIG. 4C depicts formation of partially-modulated primary-column separated sample-bearing first carrier when pulsed higher flow rate carrier enters three-way connector.

Referring to FIGS. 4a through 4c, the result of introducing modulated faster second carrier 154 and slower second carrier 152 to three-way connector 60 is depicted in a negative pulse mode. FIG. 4a shows faster second carrier 154 and primary-column-separated sample-bearing first carrier 110 entering three-way connector 60 through entrance ports 66 and 64 respectively. Within exit port 62, primary-column-separated sample-bearing first carrier 110 and faster second carrier 154 mingle to form more-diluted primary-column-separated sample-bearing first carrier 160.

FIG. 4b depicts slower second carrier 152, which flows at a rate sufficient to prevent upstream contamination into entrance port 66, and primary-column-separated sample-bearing first carrier 110 entering entrance ports 66 and 64 respectively. The flow rate of slower second carrier 152 should be low enough to permit detection of compounds in the sample by detector 80.

FIG. 4c shows the effect of re-introduction of the faster second carrier 154. Primary-column-separated sample-bearing first carrier 110 is again diluted to form more-diluted primary-column-separated sample-bearing first carrier 160. Less diluted primary-column-separated sample-bearing first carrier 110 becomes packet 165. Packet 165 is bounded by volumes of higher dilution caused when faster second carrier 154 is cyclically added to primary-column-separated sample-bearing first carrier 110.

Because the second carrier 150 is fed into three-way connector 60 with alternate flow rates and because primary-column-separated sample-bearing first carrier 110 continuously flows from primary column 30 through three-way connector 60, the resulting stream is continuous. As a result, primary-column-separated sample-bearing first carrier 110 is now partially modulated between volumes of more-diluted primary-column-separated sample-bearing first carrier 160 and packet 165, collectively forming partially-modulated carrier 170.

Negative pulse mode is characterized by cycling the second carrier 150 flow rate from a high flow rate for a long duration of time to a low flow rate for a short duration of time. The short duration of time slower second carrier 152 enters entrance port 66 results in a small packet 165 of less diluted primary-column-separated sample-bearing first carrier 110 exiting three-way connector 60.

Positive pulse mode is characterized by cycling the second carrier 150 flow rate from a low flow rate for a long duration of time to a high flow rate for a short duration of time. The short duration of time over which faster second carrier 154 enters entrance port 66 results in a longer packet of less dilute primary-column-separated sample-bearing first carrier 110.

Partially-modulated carrier 170 enters secondary column 70. In the preferred embodiment, secondary column 70 contains a stationary phase different from the stationary phase of primary column 30, such that primary column 30 and secondary column 70 are orthogonal and the separation in secondary column 70 is faster than the separation in primary column 30. Alternatively, different temperatures in the first column 30 and second column 70 could achieve the desired difference in separation speed. Through secondary column 70, the compounds in partially-modulated carrier 170 further separate. The partially-modulated, second-column-separated partially-modulated carrier 180 exits column 70.

At the exit of secondary column 70, a detector 80 reads intensity levels of the compounds in second-column-separated partially-modulated carrier 180 at a predetermined frequency. The frequency of the detector 80 readings should be adjusted so that there are sufficient readings per modulation. More readings result in improved accuracy in interpreting the results of the two dimensional chromatography.

Results of Partial Modulation Compared with Full Modulation

Figure 5A:
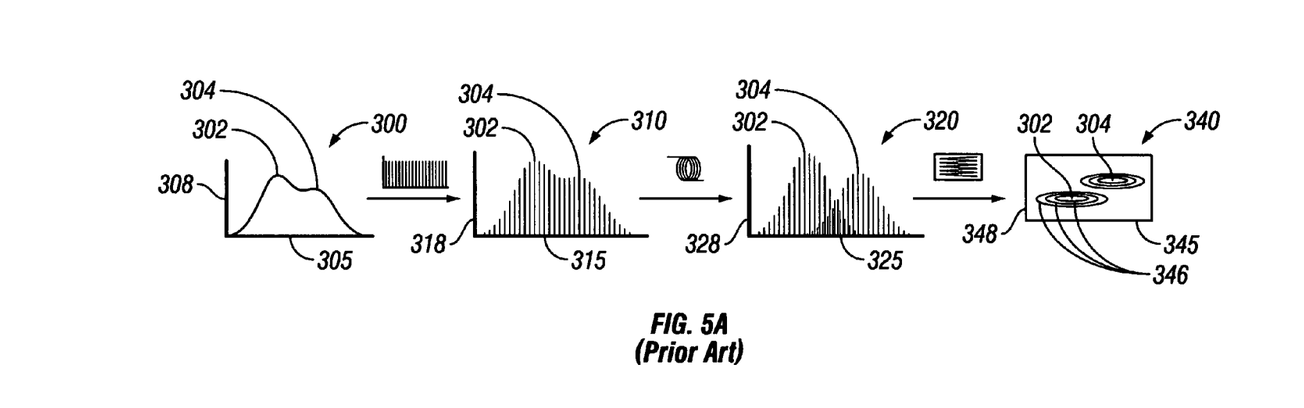
FIG. 5A is a series of graphs of a fully modulated sample-bearing first carrier undergoing two-dimensional chromatography.

FIG. 5A graphically shows the results of two-dimensional gas chromatography with full modulation. Analog graph 300 shows peaks of multiple compounds at the conclusion of a first dimension of separation. The x-axis 305 indicates the primary retention time, or the time in which a particular compound is retained in the first column. The y-axis 308 indicates the intensity of the compounds detected. Interpretation of the data at this point is difficult because the primary retention times of the analyzed compounds are similar. The distributions of the intensity of the compounds present after single dimension gas chromatography overlap, making it difficult to discern the curve of one compound from that of the other compound. Two peaks 302 and 304 can be discerned, however the individual curves are indistinguishable.

In the prior art, the analyte-bearing sample, which has been separated in the first column, is fully modulated. Modulated graph 310 shows the result of fully modulating the analyte-bearing sample between the exit of the primary column 30 and the entrance of secondary column 70. The x-axis 315 represents the primary retention time and the y-axis 318 represents the intensity of the detected compounds. Two peaks 302 and 304 are still discernable, but the curves associated with the individual compounds are still obscured.

The fully modulated analyte-bearing sample enters secondary column 70, where the compounds in the analyte-bearing sample are further separated by an orthogonal means of chromatography. Detector 80 senses the intensity of compounds exiting secondary column 70. The results of the chromatogram after two dimensions of separation and modulation of the analyte-bearing sample are shown on detector graph 320. The x-axis 325 and y-axis 328 still represent retention time and intensity as in the previous graphs. Because the sample analyte-bearing sample underwent an orthogonal means of separation, peaks 302 and 304 are easier to distinguish, as is most of the curve associated with each peak.

Further improvement in the interpretation of data may be found by looking at the data generated as depicted in contour graph 340. The x-axis 345 of contour graph 340 represents the primary retention time, or the time the sample was retained in the chromatograph. The y-axis 348 represents the secondary retention time, or the time between modulations. Each of the contour lines 346 represents different intensity levels. The area inside the center-most contour line represents the peak 302 or 304 of the detected compound. By graphically depicting the detected intensity levels in two time dimensions, the chromatographer may more easily discern the compounds present and detected in the sample.

Figure 5B:
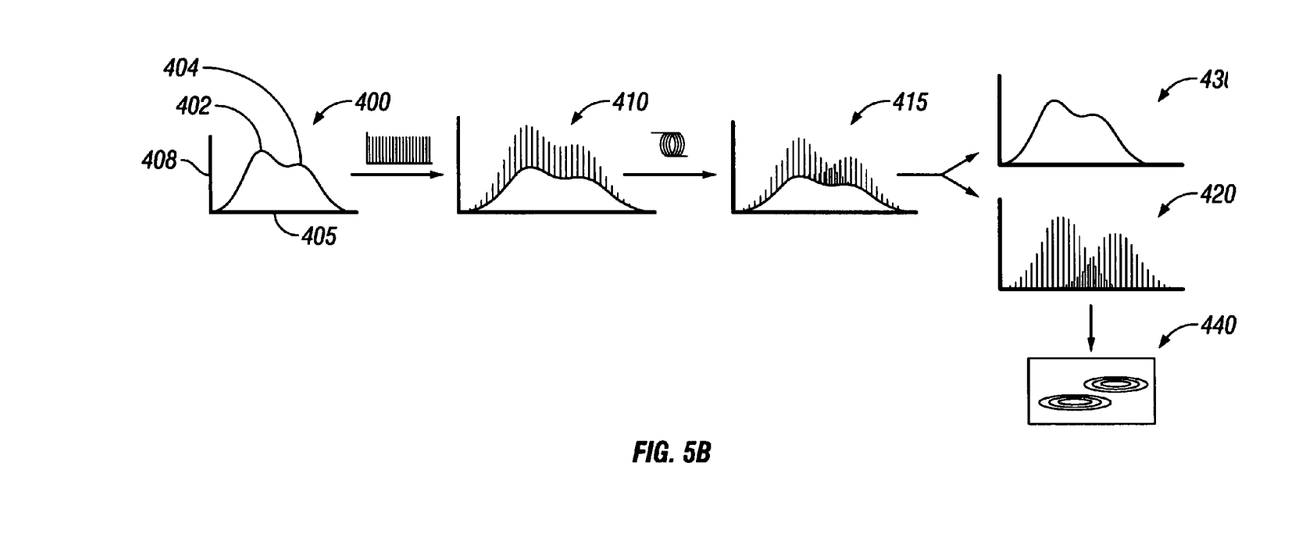
FIG. 5B is a series of graphs of a partially modulated analyte-bearing sample undergoing two-dimensional chromatography.

FIG. 5B graphically shows the results of two-dimensional chromatography with partial modulation. Analog graph 400 has the same characteristics as analog graph 300, where the x-axis 405 represents retention time and the y-axis 408 represents intensity of the detected compounds. Two peaks 402 and 404 are somewhat discernable, but the curves are overlapping to such an extent that they are not clearly identifiable.

The analyte-bearing sample is partially modulated by alternately introducing a faster and slower second carrier. The result of partially modulating the analyte-bearing sample is depicted in partial modulation graph 410.

The partially modulated analyte-bearing sample is passed through a second dimension of chromatography, where the compounds in the analyte-bearing sample are further separated. Detection graph 415 shows that the analyte-bearing sample exiting the second column contains diluted compound alternated with packets of concentrated compound. Spikes occur where the detector processes the sharper pulses, or packet, of concentrated compound. The secondary signal 430 and primary signal 420 may then be separated from detection gravh 415, permitting creation of contour granh 440 from primary signal 420.

The partially modulated analyte-bearing sample contains the same information as the fully modulated analyte-bearing sample. The contour graph 440 resulting from partial modulation depicts the same information as contour graph 340 resulting from full modulation.

The use of partial modulation with comprehensive two-dimensional chromatography allows faster second dimension separation than the use of full modulation. The speed in which more-diluted primary-column-separated sample-bearing first carrier 160 and packet 165 are transferred through the second column 70 may be faster than that possible with full modulation of the analyte-bearing sample.

Figure 6A:
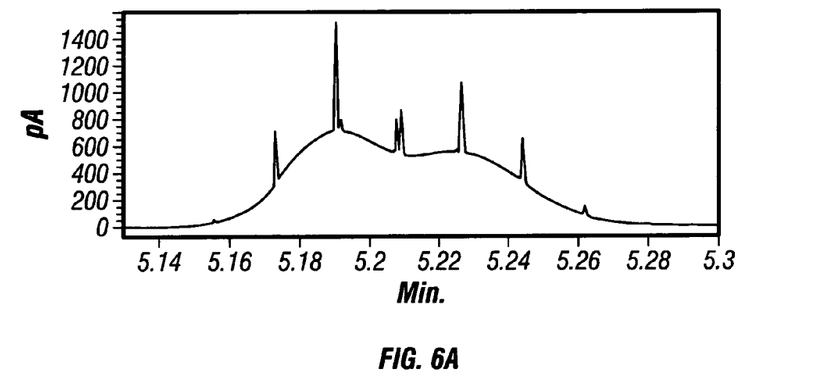
FIG. 6A depicts the results of chromatography on a partially-modulated analyte-bearing sample in the negative pulse mode.
Figure 6B:
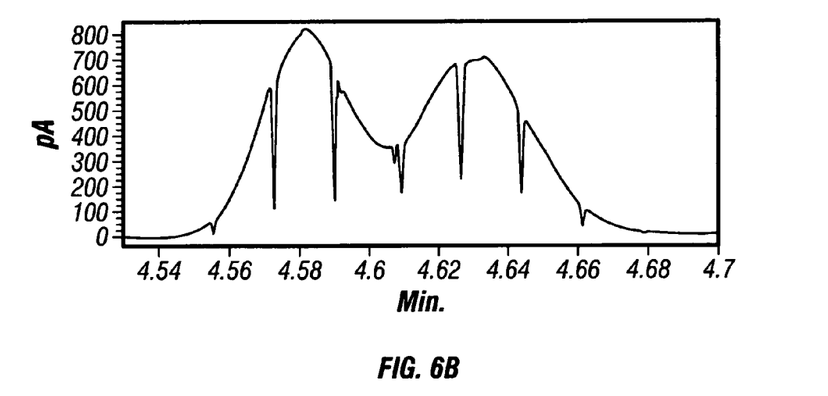
FIG. 6B depicts the results of chromatography on a partially-modulated analyte-bearing sample in the positive pulse mode.

FIGS. 6A and 6B depict the difference in the detection of compounds between partial modulation in negative pulse mode and positive pulse mode. After separation in second column 70, detector 80 outputs signals associated with compounds present in the analyte. The signal associated with each compound is separated by the signal associated with the second carrier.

FIG. 6A shows the chromatographic result of using negative pulse mode partial modulation. In negative pulse mode, the intensity of the signal associated with each compound in concentrated primary-column-separated sample-bearing first carrier 110 will be greater than and in addition to the signal associated with second carrier 150 and highly diluted primary-column-separated sample-bearing first carrier 110.

FIG. 6B shows the chromatographic result of using positive pulse mode partial modulation. In positive pulse mode, the intensity of the signal associated with each compound in concentrated primary-column-separated sample-bearing first carrier 110 will be less than and in opposition to the signal associated with second carrier 150 and highly diluted primary-column-separated sample-bearing first carrier 110.

The foregoing description of the invention illustrates a preferred embodiment thereof. Various changes may be made in the details of the illustrated construction within the scope of the appended claims without departing from the true spirit of the invention. The present invention should only be limited by the claims and their equivalents.

What is claimed is:

1. A method of chromatographically separating a sample, said sample containing an analyte, said sample being in a first carrier, comprising:
   separating said sample in a primary column;
   modulating a second carrier repeatedly and continuously to cycle at a fixed rate of time between a primary flow rate and a secondary flow rate, said second carrier primary flow rate and second carrier secondary flow rate being unequal;
   continuously introducing said modulated second carrier to said separated sample-bearing first carrier, thereby partially modulating said separated sample-bearing first carrier; and
   further separating said partially modulated separated sample-bearing first carrier in a secondary column.

2. The method of claim 1, in which said partial modulation comprises:
   positive pulse mode, wherein said primary flow rate of said second carrier is provided for a longer period of time than said secondary flow rate of said second carrier.

3. The method of claim 1, in which said partial modulation comprises:
   negative pulse mode, wherein said primary flow rate of said second carrier is provided for a shorter period of time than said secondary flow rate of said second camer.

4. The method of claim 1, wherein said primary flow rate of said second carrier is sufficient to prevent upstream commingling of said second carrier with said sample-bearing first carrier.

5. A method for chromatographically separating components of a sample, said sample containing an analyte, said sample being in a first carrier, comprising:
   injecting said sample-bearing first carrier into a primary column, such that the sample-bearing first carrier migrates through said primary column;
   said sample bearing first carrier at least partially separated in said first column;
   said at least partially-separated sample transmitted to a three-way connector first entrance port;
   providing a primary flow rate of a second carrier through a second entrance port of said three-way connector sufficient to prevent upstream commingling of said second carrier with said sample-bearing first carrier;
   providing a secondary flow rate of said second carrier through said three-way connector second entrance port sufficient to distinguishably dilute said separated sample-bearing first carrier;

modulating said second carrier to continuously and repeatedly cycle at a fixed rate of time between said primary flow rate and said secondary flow rate, said second carrier primary flow rate and second carrier secondary flow rate being unequal, continuously introducing said modulated second carrier to said separated sample-bearing first carrier, producing a partially modulated sample-bearing first carrier with each modulation of said second carrier; and feeding said partially modulated sample-bearing first carrier through an exit port of said three-way connector into a secondary column, wherein said sample undergoes further separation.

6. The method of claim 5, in which said partial modulation comprises:

positive pulse mode, wherein said primary flow rate of said second carrier is provided for a longer period of time than said secondary flow rate of said second carrier.

7. The method of claim 5, in which said partial modulation comprises:

negative pulse mode, wherein said primary flow rate of said second carrier is provided for a shorter period of time than said secondary flow rate of said second carrier.

* * * * *